United States Patent

Takemoto et al.

[11] Patent Number: 5,795,612
[45] Date of Patent: Aug. 18, 1998

[54] ASPARTYLDIPEPTIDEAMINE DERIVATIVES AND SWEETNER

[75] Inventors: Tadashi Takemoto; Yusuke Amino; Ryoichiro Nakamura, all of Kawasaki, Japan

[73] Assignee: Ajinomoto Co., Inc., Tokyo, Japan

[21] Appl. No.: 579,976

[22] Filed: Dec. 28, 1995

[30] Foreign Application Priority Data

Jun. 12, 1995 [JP] Japan ................ 7-144844

[51] Int. Cl.⁶ ............... A23L 1/236; C07C 229/00
[52] U.S. Cl. ............... 426/548; 562/433; 562/442; 562/450
[58] Field of Search ............ 426/548; 562/450, 562/442, 433

[56] References Cited

U.S. PATENT DOCUMENTS

| | | | |
|---|---|---|---|
| 5,286,509 | 2/1994 | D'Angelo et al. | 426/548 |
| 5,616,761 | 4/1997 | Takemoto et al. | 562/450 |
| 5,629,450 | 5/1997 | Hijiya et al. | 564/425 |

FOREIGN PATENT DOCUMENTS

| | | |
|---|---|---|
| 0 691 346 | 1/1996 | European Pat. Off. . |
| WO 94/00028 | 1/1994 | WIPO . |

*Primary Examiner*—Leslie Wong
*Attorney, Agent, or Firm*—Oblon, Spivak, McClelland, Maier & Neustadt, P.C.

[57] ABSTRACT

Novel aspartyldipeptideamide derivatives of formula (I):

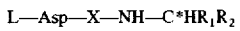

L—Asp—X—NH—C*HR₁R₂ and salts thereof, wherein X is a D-α-amino acid residue or a DL-α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenyl glycine and D- or DL furyl glycine, or X is a cyclic or non-cyclic α, α-dialkyl amino acid residue having 3 to 6 carbon atoms; $R_1$ is a linear or branched alkyl group having 1 to 6 carbon atoms or an alkoxymethyl group having 2 to 7 carbon atoms in the alkoxy portion; $R_2$ is a phenyl group having a substituent in its 2, 3- or 4-position selected from the group consisting of F, Cl, Br, I, a hydroxy group, a linear or branched alkoxy group having 1 to 6 carbon atoms, a cyano group, a nitro group, an acetyl group, an amino group and an acetylamino group, or $R_2$ is a phenyl group having a methylenedioxy group, a trimethylene group or a tetramethylene group in its 2, 3- or 3, 4- position or $R_2$ is a 2, 3- or 4-pyridyl group, a 2- or 3-furyl group or a 2- or 3-thienyl group; the configuration of C* in formula (I) is (S) or (RS) when $R_1$ is a linear or branched alkyl group; (R), (S), or (RS) when $R_1$ is an alkoxymethyl group; and in formula (I), L-Asp and X are α-bonded.

11 Claims, No Drawings

ASPARTYLDIPEPTIDEAMINE DERIVATIVES AND SWEETNER

FIELD OF THE INVENTION

This invention relates to novel aspartyldipeptideamide derivatives, their salts and a sweetener containing them as an active ingredient.

BACKGROUND OF THE INVENTION

In recent years, with the advancement of diet, much more sugar has been consumed than required and obesity and subsequent disease have become a social problem, creating a demand for a low calorie sweetener in place of sugar. Aspartame is a superior, popular sweetener in terms of safety and sweet taste quality, but has a problem in stability. To improve stability and increase sweetness potency, an amide derivative of an aspartyl-D-amino acid not having an ester bonding was studied and compounds described, for example, in U.S. Pat. Nos. 4,411,925 or 5,286,509 were found.

OBJECT OF THE INVENTION

One object of the invention is to provide novel aspartyldipeptide derivatives and their salts.

Another object is to provide novel aspartyldipeptide derivatives and their salts using an amino acid component and an amine component.

Another object is to provide novel aspartyldipeptide derivatives and their salts which are highly stable, safe and made from easily available starting materials.

Another object of the invention is to provide a sweetner comprising novel aspartyldipeptide derviatives and/or their physiologically acceptable salts.

Other objects will be apparent as the invention becomes better understood by reference to the following description.

DESCRIPTION OF THE INVENTION

The above objects are provided by the following aspartyldipeptideamide derivatives of formula (I), which are excellent in both stability and sweet taste quality:

$$L\text{—Asp—}X\text{—NH—}C^*HR_1R_2 \quad (I)$$

wherein X is a D-α-amino acid residue or a DL-α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenyl glycine and D- or DL furyl glycine, or X is a cyclic or non-cyclic α,α-dialkyl amino acid residue having 3 to 6 carbon atoms; $R_1$ is a linear or branched alkyl group having 1 to 6 carbon atoms or an alkoxymethyl group having 2 to 7 carbon atoms in the alkoxy portion; $R_2$ is a phenyl group having a substituent in its 2, 3- or 4-position selected from the group consisting of F, Cl, Br, I, a hydroxy group, a linear or branched alkoxy group having 1 to 6 carbon atoms, a cyano group, a nitro group, an acetyl group, an amino group and an acetylamino group, or $R_2$ is a phenyl group having a methylenedioxy group, a trimethylene group or a tetramethylene group in its 2, 3- or 3, 4-position or $R_2$ is a 2, 3- or 4-pyridyl group, a 2- or 3-furyl group or a 2- or 3-thienyl group; the configuration of C* of formula (I) is (S) or (RS) when $R_1$ is a linear or branched alkyl group; (R), (S), or (RS) when $R_1$ is an alkoxymethyl group; and in formula (I), L-Asp and X are α-bonded. For example, when X is D-valine, $R_1$ is ethyl and $R_2$ is 4-hydroxyphenyl, the compound of formula (I) has the following structure: $H_2NCH(CH_2COOH)CONHCH(CH(CH_3)_2)CONHC^*H(Et)(C_6H_4OH)$, where C* is (S) or (RS). Optical purity (ee) preferably ranges from >50%, more preferably >70% and is, most preferably, 80, 85, 90, 95 or 100% including all values therebetween.

Salts of compounds of formula (I) are also included in this invention, including salts of alkaline metals such as sodium and potassium, salts of alkaline earth metals such as Ca and Mg, salts of amines such as monoethanolamine, salts of inorganic acids such as hydrochloric acid and sulfuric acid and salts of organic acids such as citric acid and acetic acid. Physiologically acceptable salts are prefered.

The aspartyldipeptide derivative of this invention can be obtained by conventional peptide synthesis well within the skill of the average artisan. See Izumiya et. al., *Basics of Peptide Synthesis and Experiments*: Maruzen, Jan. 20, 1985, incorporated herein by reference. After condensation of an α-amino acid in which an amino group was protected with a corresponding amine, the protective group was removed: α-L-aspartyl-α-amino acid amides can be obtained by preparing a dipeptideamide by condensation of an α-amino acid amide and an L-aspartic acid in which a β-carboxyl group and an amino group are protected, and then removing the protected groups or by reacting and active ester of an L-aspartic acid in which β-carboxyl group and an amino group are protected with an α-amino acid, then reacting the resulting protected dipeptide with an amine and removing the protected groups. The methods of preparing the compounds of this invention are not limited to the methods described above, however, and include those described in U.S. Ser. No. 08/579,975 incorporated herein by reference.

The β-alkoxyamine of this invention can be easily obtained as an optically active substance by the method proposed by A. I. Meyere et. al. (*Journal of Organic Chemistry* 43, 892, 1978), incorporated herein by reference and it can be synthesized otherwise. The optically active benzylamine derivatives can be obtained by the method described by C. K. Miao et. al. (*Tetrahedron Letters*, 34, 2259, 1993) incorporated herein by reference, and the references cited therein.

Sensory evaluation have shown the compounds of formula (I) and their salts to have a similar sweet taste quality to sugar and a strong sweetness potency. For example, α-L-aspartyl-D-α-aminobutyric acid (S)-α-ethyl-p-hydroxybenzylamide has a sweetness potency of 2000 (sugar=1), α-L-aspartyl-D-valine (S)-α-ethyl-p-hydroxybenzylamide has a sweetness potency as 1500 (sugar=1), α-L-aspartyl-D-valine (S)-α-ethyl-p-chlorobenzylamide has sweetness potency as 1250 (sugar=1), α-L-aspartyl-D-α-aminobutyric acid (R)-α-methoxymethyl-p-hydroxybenzylamide (optical purity of amine: 85% ee) has sweetness potency as 1500 (sugar=1), α-L-aspartyl-D-valine (R)-α-methoxymethyl-p-hydroxybenzylamide (optical purity of amine: 85% ee) has sweetness potency as 1250 (sugar=1). The half-life of a valine derivative was 8 to 9 days (aspartame: approximately 1 day) heated to 70° C. in a phosphate buffer (pH=3).

The compounds of this invention have good sweetness multiples and good sweet taste quality without unfavorable qualities such as bitterness and aftertaste.

The structure and sensory evaluation results of some synthesized invention aspartyldipeptide derivatives are shown in Table 1.

TABLE 1

The Structure of Aspartyldipeptide
Derivatives and Their Sweetness Potency

| X | C* Conformation | Optical Purity % ee | $R_1$ | $R_2$ | Sweetness Potency[1] |
|---|---|---|---|---|---|
| D-Abu[2] | (S) | >95 | Et | $C_6H_5$-p-OH | 2000 |
| D-Val | (S) | >95 | Et | $C_6H_5$-p-OH | 1500 |
| D-Val | (S) | >95 | Et | $C_6H_5$-p-Cl | 1250 |
| D-Val | (S) | 70 | Me | $C_6H_5$-p-OH | 1000 |
| D-Val | (S) | >95 | Et | $C_6H_5$-p-$^i$Pr | 0 |
| D-Val | (S) | 90 | Et | 4-pyridyl | 300 |
| D-Abu | (R) | 85 | OMe | $C_6H_5$-p-OH | 1500 |
| D-Val | (R) | >90 | OMe | $C_6H_5$-p-OH | 1250 |
| D-Val | (R) | >95 | OMe | $C_6H_5$-p-OMe | 250 |
| D-Val | (RS) |  | OMe | 2-Furyl | 200 |

[1] Compared with 4% aqueous sucrose solution.
[2] Abu = α-aminobutyric acid.

The compounds of the invention and their salts, preferably their physiologically acceptable salts, can be mixed with other sweeteners unless otherwise specified, and can be used as sweeteners alone or in combination of one or more, and can be mixed with carriers, diluents, etc. common to the sweetner art. Sweetners containing the invention compound (s) preferably comprise an amount of said compound(s) sufficient to impart a sweet taste when eaten. Particularly preferred compounds of the invention have sweetness multiples as measured in Table 1 above of at least 100, including 200, 300, 400, 500, 600, 700, 800, 900, 1000, 2000 and 3000 and all values therebetween.

EXAMPLE

Example 1

Synthesis of an α-L-aspartyl-D-α-aminobutyric acid (S)-α-ethyl-p-hydroxybenzylamide 1.37 g (3.1 mmol) of N-benzyloxycarbonyl-β-O-benzyl-L-aspartyl-D-α-aminobutyric acid and 0.74 g (3.08 mmol; optical purity >95% ee) of (S)-α-ethyl-p-benzyloxybenzylamine were dissolved into 30 ml of methylene chloride (Solution I); 0.65 g (3.4 mmol) of water-soluble carbodiimide hydrochloride and 0.46 g (3.4 mmol) of HOBt were added to Solution I under cooling and the mixture was stirred for one hour under cooling and stirred overnight at room temperature. The reaction mixture was concentrated under reduced pressure and 100 ml of ethyl acetate was added to the residue, then the organic solution was washed twice with 50 ml of 5% aqueous solution of citric acid and washed once with 50 ml of water, washed twice with 50 ml of 5% aqueous solution of sodium hydrogencarbonate and washed with 50 ml of brine. After the organic layer was dried with anhydrous magnesium sulfate, the magnesium sulfate was filtered and the filtrate was concentrated under reduced pressure and 1.46 g (2.2 mmol) of solid N-benzyloxycarbonyl-β-O-benzyl-L-aspartyl-α-D-aminobutylic acid (S)-α-ethyl-p-benzyloxybenzylamide was obtained.

1.45 g (2.18 mmol) of N-benzyloxycarbonyl-P-O-benzyl-L-aspartyl-D-α-aminobutyric acid (S)-α-ethyl-p-benzyloxybenzylamide was dissolved into a mixture of 35 ml of methanol and 10 of water, then 0.13 ml of acetic acid was added followed by 450 mg of 5% Pd-carbon (water content 50%), and the reduction was continued for 3 hours at 50° C. under hydrogen stream. The catalyst was filtered for removal; after the filtration, the filtrate was concentrated under reduced pressure, the obtained residue was recrystallized from water and dried, and 0.44 g (1.25 mmol) of α-L-aspartyl-D-α-aminobutyric acid (S)-α-ethyl-p-hydroxybenzylamide was obtained.

$^1$HNMR ($D_2O$) δ:0.73 (t, 3H), 0.79 (t, 3H), 1.50–1.70 (m, 4H), 2.53–2.70 (m, 2H), 4.05 (t, 1H), 4.07 (t, 1H), 4.46 (t, 1H), 6.72 (d, 2H), 7.07 (d, 2H).

FAB-MS 352 ($MH^+$)

Sweetness Potency (sugar=1) 2000.

Example 2

Synthesis of α-L-aspartyl-D-α-aminobutyric acid (R)-α-methoxymethyl-p-hydroxybenzylamide Instead of using (S)-α-ethyl-p-benzyloxybenzylamine, (R)-α-methoxymethyl-p-benzyloxybenzylamine (optical purity: 85% ee) was used and the method of Example 1 was repeated. Solid α-L-aspartyl-D-α-aminobutyric acid (R)-α-methoxymethyl-p-hydroxybenzylamide was obtained at the total yield of 43.7%.

$^1$HNMR (DMSO-$d_6$) δ:0.85 (t, 3H), 1.48–1.72 (m, 2H), 2.24(dd, 1H), 2.43 (dd, 1H), 3.22 (s, 3H), 3.70 (dd, 1H), 4.20–4.32 (m, 1H), 4.91 (q, 1H), 6.70 (d, 2H), 7.11 (d, 2H), 8.37 (d, 1H), 8.38–8.47 (m, 1H).

FAB-MS 368 ($MH^+$)

Sweetness Potency (sugar=1) 1500.

Example 3

Synthesis of α-L-aspartyl-D-valine (S)-α-ethyl-p-hydroxybenzylamide 0.67 g (3.08 mmol) of N-t-butoxycarbonyl-D-valine and 0.74 g (3.08 mmol) of (S)-α-ethyl-p-benzyloxybenzylamine were dissolved into 25 ml of methylene chloride (Solution II), 0.59 g (3.08 mmol) water-soluble carbodiimide hydrochloride and 0.42 g (3.08 mmol) HOBt were added to the solution II under cooling and stirred for one hour under cooling, and stirred overnight at room temperature. The reaction mixture was concentrated under reduced pressure and 50 ml of aqueous solution of 5%. citric acid was added to the residue, which was extracted twice with 50 ml of ethyl acetate, then the organic layer was washed with 20 ml of water, and 25 ml of 5% aqueous solution of sodium hydrogencarbonate and 20 ml of brine. After the organic layer was dried with anhydrous magnesium sulfate and filtered, the filtrate was concentrated under reduced pressure and 1.12 g (2.54 mmol) of solid N-t-butoxycarbonyl-D-valine (S)-α-ethyl-p-benzyloxybenzylamide was obtained.

13 ml of 4N-HCl/dioxane was added to 1.11 g (2.52 mmol) of N-t-butoxycarbonyl-D-valine (S)-α-ethyl-p-benzyloxybenzylamide and the solution was stirred for one hour at room temperature. The reaction solution was concentrated under reduced pressure and 30 ml of ether was added to the residue and further concentrated. 25 ml of methylene chloride and 0.39 ml (2.77 mmol) of triethylamine were added for dissolution and 0.99 g (2.77 mmol) of N-benzyloxycarbonyl-L-aspartic acid-β-benzylester was added after dissolution (Solution III). During the cooling period, 0.53 g (2.77 mmol) of water-soluble carbodiimide hydrochloride and 0.37 g (2.77 mmol) of HOBt were added and stirred for one hour under cooling and continued stirring overnight. The reaction mixture was concentrated under reduced pressure and 50 ml of aqueous solution of 5% citric acid was added to the residue, which was extracted twice with ethyl acetate then the organic layer was washed with 20 ml of water, 25 ml of 5% sodium hydrogencarbonate aqueous solution and 20 ml of brine. After the organic layer was dried with anhydrous magnesium sulfate and filtered, the filtrate was concentrated under reduced pressure and 1.47 g (2.16 mmol) of solid N-benzyloxycarbonyl-β-O-benzyl-L-aspartyl-D-valine (S)-α-ethyl-p-benzyloxybenzylamide was obtained.

1.46 g (2.16 mmol) of N-benzyloxycarbonyl-β-O-benzyl-L-aspartyl-D-valine (S)-α-ethyl-p-benzyloxybenzylamide was dissolved into a mixture of 30 ml of methanol and 5 ml of water, then 0.45 g of 5% Pd-carbon (water content 50%) and acetic acid were added and were reduced for 4 hours under hydrogen flow at 50° C. After adding 40 ml of water, the catalyst was filtered for removal and the filtrate was concentrated to approximately 25% under reduced pressure and was filtered to separate crystals and dried to obtain 0.42 g (1.15 mmol) of α-L-aspartyl-D-valine (S)-α-ethyl-p-hydroxybenzylamide.

$^1$HNMR (DMSO-d$_6$) δ:0.76 (m, 9H), 1.59–1.68 (m, 2H), 1.90–2.01 (m, 1H), 2.21 (dd, 1H), 2.42 (dd, 1H), 3.75 (dd, 1H), 4.20–4.26 (m, 1H), 4.58 (q, 1H), 6.69 (d, 2H), 7.08 (d, 2H), 8.30 (d, 1H), 8.38 (d, 1H).

FAB-MS 366(MH$^+$)

Sweetness Potency (sugar=1) 1500.

Example 4

Synthesis of α-L-aspartyl-D-valine (R)-α-methoxymethyl-p-hydroxybenzylamide

Instead of using (S)-α-ethyl-p-benzyloxybenzylamine, (R)-α-methoxymethyl-p-O-benzyloxybenzylamine (optical purity approximately 85% ee) was used and the method of Example 3 was repeated. Solid α-L-aspartyl-D-valine (R)-α-methoxymethyl-p-hydroxybenzylamide was obtained at the total yield of 33.7%.

$^1$HMNR (D$_2$O) δ:0.79 (t, 6H), 1.87–1.98 (m, 1H), 2.55–2.71 (m, 2H), 3.20 (s, 3H), 3.45–3.55 (m, 2H), 3.95–4.15 (m, 2H), 4.86 (t, 1H), 6.73 (d, 2H), 7.09 (d, 2H).

FAB-MS 382 (MH$^+$)

Sweetness Potency (sugar=1) 1250.

Example 5

Synthesis of α-L-aspartyl-D-valine (R)-α-methyl-p-hydroxybenzylamide

Instead of using (S) -α-ethyl-p-benzyloxybenzylamine, (S) -α-methyl-p-benzyloxybenzylamine (optical purity approximately 70% ee) was used and the method of Example 3 was repeated. Solid α-L-aspartyl-D-valine (S)-α-methyl-p-hydroxybenzylamide was obtained at the total yield of 69.6%.

$^1$HNMR (D$_2$O) d:0.79(t,6H), 1.29(d, 3H), 1.80–1.98(m, 1H), 2.64–2.70(m, 2H), 3.92–3.95(m, 1H), 4.09–4.15(m, 1H), 4.70–4.80(m, 1H), FAB-MS 352 (MH$^+$).

Sweetness Potency (sugar=1) 1000.

Example 6

Synthesis of α-L-aspartyl-D-valine (S)-α-ethyl-p-chlorobenzylamide 0.82 g (3.77 mmol) of N-t-butoxycarbonyl-D-valine and 0.53 g (3.77 mmol; optical purity >95% ee) of (S)-α-ethyl-p-chlorobenzylamine were dissolved into 25 ml methylene chloride (Solution IV), 0.72 g (3.77 mmol) of water-soluble carbodiimide hydrochloride and 0.51 g (3.77 mmol) of HOBt were added to Solution IV under cooling and stirred for one hour under cooling, and stirred overnight at room temperature. The reaction mixture was concentrated under reduced pressure and 50 ml of aqueous solution of 5% citric acid was added to the residue, which was extracted twice with ethyl acetate then the organic layer was washed with 20 ml of water, and 25 ml of 5% sodium hydrogencarbonate aqueous solution and 20 ml of brine. After the organic layer was dried with anhydrous magnesium sulfate and filtered, the filtrate was concentrated under reduced pressure to obtain 1.04 g (2.83 mmol) of solid N-t-butoxycarbonyl-D-valine (S)-α-ethyl-p-chlorobenzylamide was obtained.

14 ml of 4N-HCl/dioxane solution was added to 1.03 g (2.80 mmol) of N-t-butoxycarbonyl-D-valine (S)-α-ethyl-p-chlorobenzylamide and the solution was stirred for one hour at room temperature. The reaction solution was concentrated under reduced pressure and 30 ml of ether was added and further concentrated. 25 ml of methylene chloride and 1.41 g (3.08 mmol) of N-t-butoxycarbonyl-L-aspartic acid-β-t-butylester DCHA salt were added. During the cooling period, 0.59 g (3.08 mmol) of water-soluble carbodiimide hydrochloride and 0.42 g (3.08 mmol) of HOBt were added and stirred for one hour under cooling and stirred overnight at room temperature. The reaction mixture was concentrated under reduced pressure and 50 ml of aqueous solution of 5% citric acid was added to the residue, which was extracted twice with ethyl acetate, then the organic layer was washed with 20 ml of water, 25 ml of 5% sodium hydrogencarbonate solution and 20 ml of brine. The organic layer was dried with anhydrous magnesium sulfate and filtered, the filtrate was concentrated under reduced pressure to obtain 1.30 g (2.41 mmol) of solid N-t-butoxycarbonyl-β-O-t-butyl-L-aspartyl-D-valine (S)-α-ethyl-pchlorobenzylamide.

10 ml of 4N-HCl dioxane solution was added to 1.30 g (2.41 mmol) of N-t-butoxycarbonyl-β-O-t-butyl-L-aspartyl-D-valine (S)-α-ethyl-p-chlorobenzylamide residue and the solution was stirred for one hour at room temperature. The reaction solution was concentrated under reduced pressure and was further concentrated with 20 ml of water and a small amount of 28% ammonia water.

The residue was dissolved into a mixture of 50 ml of water and 30 ml of methanol, and was concentrated under reduced pressure and the resulting crystals were filtered and dried to obtain 0.84 g (2.18 mmol) of α-L-aspartyl-D-valine (S)-α-ethyl-p-chlorobenzylamide.

$^1$HNMR (DMSO-d$_6$) δ:0.85 (d, 3H), 0.86 (d, 3H), 1.60–1.66 (m, 2H), 1.87–2.02 (m, 1H), 2.24 (dd, 1H), 2.44 (dd, 1H), 4.20–4.27 (m, 1H), 4.63–4.72 (m, 1H), 7.30–7.39 (m, 4H), 8.44 (brs, 1H), 8.49 (d, 1H).

FAB-MS 384(MH$^+$)

Sweetness Potency (sugar=1) 1250.

Example 7

Synthesis of α-L-aspartyl-D-valine (S)-α-4-pyridylpropylamide 1.38 g (6.35 mmol) of N-t-butoxycarbonyl-D-valine and 0.79 g (5.77 mmol; optical purity 90% ee) of (S)-α-4-pyridylpropylamine were dissolved into 40 ml of methylene chloride (Solution V), 1.22 g (6.35 mmol) water-soluble carbodiide hydrochloride and 0.86 g (6.35 mmol) of HOBt were added to Solution V under cooling and stirred for one hour under cooling and overnight at room temperature. The reaction mixture was concentrated under reduced pressure and 50 ml of aqueous solution of 5% citric acid was added to the residue, which was extracted twice with 50 ml of ethyl acetate, then the organic layer was washed with 20 ml of water, and 25 ml of aqueous solution of 5% sodium hydrogencarbonate and 20 ml of brine. After the organic layer was dried with anhydrous magnesium sulfate and filtered, the filtrate was concentrated under reduced pressure and 0.85 g (2.52 mmol) of solid N-t-butoxycarbonyl-valine (S)-α-4-pyridylpropylamide was obtained.

13 ml of 4N-HCl/dioxane solution was added to 0.85 g (2.52 mmol) of N-t-butoxycarbonyl-D-valine (S) -α-4-pyridylpropylamide and the solution was stirred for one hour at room temperature. The reaction solution was concentrated under reduced pressure and 30 ml of ether was added to the residue for further concentration. 25 ml of methylene chloride and 0.77 ml (5.56 mmol) of triethylamine were added to the residue and dissolved, then 0.99 g (2.78 mmol) of N-benzyloxylcarbonyl-L-aspartic acid-p-benzyl ester was added. Under cooling, 0.53 g (2.78 mmol) of water-soluble carbodiimide hydrochloride and 0.38 g (2.78 mmol) of HOBt were added under cooling and stirred for one hour and stirred over night at room temperature. The reaction mixture was concentrated under reduced pressure and 50 ml of 5% citric acid was added to the residue, which was extracted twice with ethyl acetate then the organic layer was washed with 20 ml of water, 25 ml of aqueous solution of 5% sodium hydrogencarbonate and 20 ml of brine. After the organic layer was dried with anhydrous magnesium sulfate and filtered, the filtrate was concentrated under reduced pressure and 1.12 g (1.95 mmol) of solid N-benzyloxycarbonyl-β-O-benzyl-L-aspartyl-D-valine (S)-α-4-pyridylpropylamide was obtained.

1.12 g (1.95 mmol) of N-benzyloxycarbonyl-β-O-benzyl-L-aspartyl-D-valine (S)-α-4-pyridylpropylamide was dissolved in a mixture of 40 ml of methanol and 5 ml of water, and 0.40 g of 5% Pd-carbon (water content 50%) was added and reduced under hydrogen flow. Adding 40 ml of water, the catalyst was filtered and removed, and the filtrate was concentrated under reduced pressure to approximately 25%, and the resulting crystals were collected and dried to obtain 0.60 g (1.70 mmol) of α-L-aspartyl-D-valine (S)-α-4-pyridylpropylamide. $^1$HNMR (DMSO-$d_6$) δ:0.83–0.90 (m, 9H), 1.63–1.74 (m, 2H), 1.95–2.06 (m, 1H), 2.66–2.78 (m, 2H), 4.01–4.05 (m, 1H), 4.25–4.33 (m, 1H), 4.70 (q, 1H), 7.31 (d, 2H) , 8.47–8.52 (m, 3H) , 8.63 (brd, 1H)

FAB-MS 351 (MH$^+$)

Sweetness Potency (sugar=1) Approximately 300.

Example 8

Synthesis of α-L-aspartyl-D-valine (R)-α-methoxymethyl-p-methoxybenzylamide

Instead of using (S)-α-4-pyridylpropylamine, (R)-α-methoxymethyl-p-methoxybenzylamine (optical purity >95% ee) was used and the method of Example 7 was repeated. Solid α-L-aspartyl-D-valine (R)-α-methoxymethyl-p-methoxybenzylamide was obtained at the total yield of 21.4%.

$^1$HNMR (DMSO-$d_6$) δ:0.84 (d, 3H) , 0.87 (d, 1H) , 1.90–2.03 (m, 1H), 2.20 (dd, 1H), 2.43 (dd, 1H), 3.23 (s, 3H), 3.39–3.50 (m, 2H), 3.69–3.76 (m, 1H), 3.72 (s, 3H), 4.20–4.26 (m, 1H), 4.94–5.03 (m, 1H), 6.88 (d, 2H), 7.25 (d, 2H), 8.43 (brs, 1H), 8.44 (d, 1H).

FAB-MS 396 (MW)

Sweetness Potency (sugar=1) Approximately 250.

Example 9

Synthesis of α-L-aspartyl-D-valine (RS)-α-furyl-β-methoxyethylamide

Instead of using (S)-α-4-pyridylpropylamine, (RS)-α-furyl-β-methoxyethylamine was used and the method of Example 7 was repeated. Solid α-L-aspartyl-D-valine (RS)-α-furyl-β-methoxyethylamide was obtained at the total yield of 55.4%.

$^1$HNMR (DMSO-$d_6$) δ:0.77–0.87 (m, 6H) , 1.90–2.00 (m, 1H), 2.17–2.30 (m, 1H), 2.40–2.50 (m, 1H), 3.22–3.27 (m, 3H), 3.53–3.58 (m, 2H), 3.75–3.80 (m, 1H), 4.20–4.30 (m, 1H), 5.05–5.17 (m, 1H), 6.27 (dd, 1H), 6.37–6.41 (m, 1H), 7.58 (d, 1H) , 8.42–8.53 (m, 2H)

FAB-MS 356 (MH$^+$)

Sweetness Potency (sugar=1) Approximately 200.

This application is based on Japanese Patent Application 144844/1995, filed Jun. 12, 1995, incorporated herein by reference.

What is claimed as new and desired to be secured by letters patent of the U.S. is:

1. Aspartyldipeptideamide compounds of formula (I):

and salts thereof, wherein X is a D-α-amino acid residue or a DL-α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenyl glycine and D- or DL furyl glycine, or X is a cyclic or non-cyclic α, α-dialkyl amino acid residue having 3 to 6 carbon atoms; $R_1$ is a linear or branched alkyl group having 1 to 6 carbon atoms or an alkoxymethyl group having 2 to 7 carbon atoms in the alkoxy portion; $R_2$ is a phenyl group having a substituent in its 2, 3- or 4-position selected from the group consisting of F, Cl, Br, I, a hydroxy group, a linear or branched alkoxy group having 1 to 6 carbon atoms, a cyano group, a nitro group, an acetyl group, an amino group and an acetylamino group, or $R_2$ is a phenyl group having a methylenedioxy group, a trimethylene group or a tetramethylene group in its 2, 3- or 3, 4- position or $R_2$ is a 2, 3- or 4-pyridyl group, a 2- or 3-furyl group or a 2- or 3-thienyl group; the configuration of C* in formula (I) is (S) or (RS) when $R_1$ is a linear or branched alkyl group; (R), (S) , or (RS) when $R_1$ is an alkoxymethyl group; and in formula (I), L-Asp and X are α-bonded.

2. The compound of claim 1, wherein X is a D-α-aminobutyric acid residue; $R_1$ is an ethyl group; $R_2$ is a p-hydroxyphenyl group; and the configuration of C* is (S).

3. The compound of claim 1, wherein X is a D-valine residue; $R_1$ is an ethyl group; $R_2$ is a p-hydroxyphenyl group; and the configuration of C* is (S).

4. The compound of claim 1, wherein X is a D-valine residue; $R_1$ is an ethyl group; $R_2$ is a p-chlorophenyl group; and the configuration of C* is (S).

5. The compound of claim 1, wherein X is a D-valine residue; $R_1$ is an ethyl group; $R_2$ is a 4-pyridyl group; and the configuration of C* is (S).

6. The compound of claim 1, wherein X is a D-α-aminobutyric acid residue; $R_1$ is a methoxymethyl group; $R_2$ is a p-hydroxyphenyl group; and the configuration of C* is (R).

7. The compound of claim 1, wherein X is a D-valine residue; $R_1$ is a methoxymethyl group; $R_2$ is a p-hydroxyphenyl group; and the configuration of C* is (R).

8. The compound of claim 1, wherein X is a D-valine residue; $R_1$ is a methoxymethyl group; $R_2$ is a p-methoxyphenyl group; and the configuration of C* is (R).

9. The compound of claim 1, wherein X is a D-valine residue; $R_1$ is a methoxymethyl group; $R_2$ is a 2-furyl group; and the configuration of C* is (S) or (RS).

10. The compound of claim 1, wherein X is a D-valine residue; $R_1$ is a methyl group; $R_2$ is a p-hydroxyphenyl group; and the configuration of C* is (S).

11. A sweetener comprising at least one aspartyldipeptideamide derivative of formula (I):

and salts thereof, wherein X is a D-α-amino acid residue or a DL-α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenyl glycine and D- or DL furyl glycine, or X is a cyclic or non-cyclic α, α-dialkyl amino acid residue having 3 to 6 carbon atoms; $R_1$ is a linear or branched alkyl group having 1 to 6 carbon atoms or an alkoxymethyl group having 2 to 7 carbon atoms in the alkoxy portion; $R_2$ is a phenyl group having a substituent in its 2, 3- or 4-position selected from the group consisting of F, Cl, Br, I, a hydroxy group, a linear or branched alkoxy group having 1 to 6 carbon atoms, a cyano group, a nitro group, an acetyl group, an amino group and an acetylamino group, or $R_2$ is a phenyl group having a methylenedioxy group, a trimethylene group or a tetramethylene group in its 2, 3- or 3, 4- position or $R_2$ is a 2, 3- or 4-pyridyl group, a 2- or 3-furyl group or a 2- or 3-thienyl group; the configuration of C* in formula (I) is (S) or (RS) when $R_1$ is a linear or branched alkyl group; (R), (S), or (RS) when $R_1$ is an alkoxymethyl group; and in formula (I), L-Asp and X are α-bonded.

* * * * *

UNITED STATES PATENT AND TRADEMARK OFFICE
CERTIFICATE OF CORRECTION

PATENT NO. : 5,795,612
DATED : August 18, 1998
INVENTOR(S) : Tadashi TAKEMOTO, et al.

It is certified that error appears in the above-identified patent and that said Letters Patent is hereby corrected as shown below:

On the title page, item [54] and col. 1, the first word on the title, is incorrect. It should be:

--ASPARTYLDIPEPTIDEAMIDE--

Signed and Sealed this

Twentieth Day of April, 1999

Attest:

Attesting Officer

Q. TODD DICKINSON

Acting Commissioner of Patents and Trademarks